United States Patent
Benaron et al.

(10) Patent No.: US 7,813,778 B2
(45) Date of Patent: Oct. 12, 2010

(54) IMPLANTABLE TISSUE ISCHEMIA SENSOR

(75) Inventors: David A. Benaron, Portola Valley, CA (US); Ilian H. Parachikov, Belmont, CA (US); Michael R. Fierro, Los Gatos, CA (US)

(73) Assignee: Spectros Corporation, Portola Valley, CA (US)

(*) Notice: Subject to any disclaimer, the term of this patent is extended or adjusted under 35 U.S.C. 154(b) by 764 days.

(21) Appl. No.: 11/193,071

(22) Filed: Jul. 29, 2005

(65) Prior Publication Data

US 2007/0027371 A1   Feb. 1, 2007

(51) Int. Cl.
*A61B 5/00* (2006.01)
(52) U.S. Cl. ...................... 600/323; 600/476
(58) Field of Classification Search ........................ None
See application file for complete search history.

(56) References Cited

U.S. PATENT DOCUMENTS

| | | | |
|---|---|---|---|
| RE29,304 E | 7/1977 | Greenfield et al. | |
| 4,164,374 A | 8/1979 | Lambe et al. | |
| 4,427,889 A | 1/1984 | Müller | |
| 4,513,751 A | 4/1985 | Abe et al. | |
| 4,660,974 A | 4/1987 | Machler et al. | |
| 4,697,593 A | 10/1987 | Evans et al. | |
| 5,040,533 A * | 8/1991 | Fearnot | 607/22 |
| 5,135,004 A | 8/1992 | Adams et al. | |
| 5,190,040 A | 3/1993 | Aoyagi | |
| 5,199,428 A | 4/1993 | Obel et al. | |
| 5,259,052 A | 11/1993 | Briggs et al. | |
| 5,280,788 A | 1/1994 | Janes et al. | |
| 5,318,022 A | 6/1994 | Taboada et al. | |
| 5,329,922 A | 7/1994 | Atlee, III | |
| 5,355,425 A | 10/1994 | Braiman et al. | |
| 5,357,954 A | 10/1994 | Shigezawa et al. | |
| 5,417,207 A | 5/1995 | Young et al. | |
| 5,520,190 A * | 5/1996 | Benedict et al. | 600/513 |
| 5,645,059 A | 7/1997 | Fein et al. | |
| 5,672,875 A | 9/1997 | Block et al. | |
| 5,696,861 A | 12/1997 | Schimmeyer et al. | |

(Continued)

FOREIGN PATENT DOCUMENTS

EP   1111333 A1   6/2001

(Continued)

OTHER PUBLICATIONS

Benaron, D., "Continuous, Noninvasive, and Localized Microvascular Tissue Oximetry Using Visible Light Spectroscopy," Anesthesiology, vol. 100, No. 6, Jun. 2004, pp. 1469-1475.

(Continued)

*Primary Examiner*—Carl H. Layno
*Assistant Examiner*—Jon-Eric C. Morales
(74) *Attorney, Agent, or Firm*—Nixon Peabody LLP (57) ABSTRACT

An implantable ischemia detection system in which a white LED (105) produces a continuous, visible, broadband light illuminating a target site (125). Light backscattered by the target is collected by a sensor (155), allowing for an index of ischemia to be determined, and subsequently transmitted by a sending unit (167). Power is provided by an internal power source (179). The entire implantable device is encapsulated by a biocompatible shell (102) to add long-term safety with regard to implantation.

18 Claims, 4 Drawing Sheets

U.S. PATENT DOCUMENTS

| | | | |
|---|---|---|---|
| 5,733,313 A * | 3/1998 | Barreras et al. ............... 607/33 |
| 5,743,261 A | 4/1998 | Mainiero et al. |
| 5,769,791 A | 6/1998 | Benaron et al. |
| 5,830,132 A | 11/1998 | Robinson |
| 5,830,137 A | 11/1998 | Scharf |
| 5,833,603 A * | 11/1998 | Kovacs et al. ............... 600/317 |
| 5,901,261 A | 5/1999 | Wach |
| 5,902,235 A | 5/1999 | Lewis et al. |
| 5,931,779 A | 8/1999 | Arakaki et al. |
| 5,941,822 A | 8/1999 | Skladnev et al. |
| 5,974,210 A | 10/1999 | Alcock et al. |
| 5,987,346 A | 11/1999 | Benaron et al. |
| 6,043,893 A | 3/2000 | Treiman et al. |
| 6,119,031 A | 9/2000 | Crowley |
| 6,122,536 A | 9/2000 | Sun et al. |
| 6,134,460 A * | 10/2000 | Chance ....................... 600/342 |
| 6,167,297 A | 12/2000 | Benaron |
| 6,226,082 B1 | 5/2001 | Roe et al. |
| 6,251,068 B1 | 6/2001 | Akiba et al. |
| 6,252,254 B1 | 6/2001 | Soules |
| 6,256,524 B1 | 7/2001 | Walker et al. |
| 6,277,078 B1 | 8/2001 | Porat et al. |
| 6,278,889 B1 | 8/2001 | Robinson |
| 6,353,226 B1 | 3/2002 | Khalil |
| 6,381,018 B1 | 4/2002 | Bigio et al. |
| 6,527,729 B1 | 3/2003 | Turcott |
| 6,532,381 B2 | 3/2003 | Bayer et al. |
| 6,533,466 B1 | 3/2003 | Smith |
| 6,550,979 B1 | 4/2003 | Fleenor et al. |
| 6,588,938 B1 | 7/2003 | Lambert et al. |
| 6,599,025 B1 | 7/2003 | Deutsch |
| 6,612,857 B2 | 9/2003 | Tolmie |
| 6,615,065 B1 | 9/2003 | Barrett et al. |
| 6,662,033 B2 | 12/2003 | Casciani et al. |
| 6,711,426 B2 | 3/2004 | Benaron et al. |
| 6,842,635 B1 | 1/2005 | Parker |
| 6,859,658 B1 | 2/2005 | Krug |
| 6,921,920 B2 | 7/2005 | Kazakevich |
| 6,944,488 B2 | 9/2005 | Roberts |
| 7,062,306 B2 | 6/2006 | Benaron |
| 2002/0082488 A1 | 6/2002 | Ali |
| 2004/0122478 A1 | 6/2004 | Stadler et al. |
| 2004/0218873 A1 | 11/2004 | Nagashima et al. |
| 2004/0220460 A1 | 11/2004 | Roberts |
| 2005/0010113 A1 | 1/2005 | Hall |
| 2006/0105319 A1 | 5/2006 | Rees et al. |
| 2007/0015981 A1 * | 1/2007 | Benaron et al. ............. 600/323 |
| 2007/0016080 A1 | 1/2007 | Alfano et al. |

FOREIGN PATENT DOCUMENTS

| | | |
|---|---|---|
| EP | 1094746 B1 | 10/2002 |
| EP | 0926981 B1 | 3/2004 |
| WO | WO 00/01295 | 1/2000 |
| WO | WO 00/64534 | 11/2000 |
| WO | WO 03/003914 A1 | 1/2003 |
| WO | WO 2004/058344 | 7/2004 |

OTHER PUBLICATIONS

International Search Report and Written Opinion for International Application PCT/US2006/029615, mailed Apr. 4, 2007.

Supplemental European Search Report for EP 03718250.8 dated Jan. 30, 2008.

International Search Report and Written Opinion for PCT/2003/10674 dated Nov. 25, 2003.

International Search Report and Written Opinion for PCT/2008/057096 dated Jul. 31, 2008.

International Search Report and Written Opinion for PCT/2007/013779 dated Oct. 14, 2008.

* cited by examiner

IMPLANTABLE TISSUE ISCHEMIA SENSOR

FIELD OF THE INVENTION

The present invention relates to implantable devices and methods for providing localized measurements of tissue ischemia, and more particularly relates to the embedding of a visible light source, a sensor, a power source, and a transmitter into a long-term implantable shell for the purpose of performing real-time spectroscopic analysis of in vivo tissue perfusion sensitive to local tissue ischemia.

BACKGROUND OF THE INVENTION

The clinical detection of ischemia—an insufficient delivery of oxygen to meet a tissue's metabolic needs—is unreliable. Ischemia is especially difficult to detect when the ischemia is due to a localized interruption of blood flow—such as during a heart attack or stroke. Existing laboratory tests for ischemia, such as serum enzyme-leakage tests (e.g., for tests for cardiac isoenzymes after a heart attack) or EKG electrical tests, are insensitive indicators of such local tissue ischemia, especially during the early stages. Similarly, blood tests are also insensitive to local ischemia, as the ischemia is a result of low oxygenation in a local tissue, which is reflected in the local capillary oxygenation, not in the oxygenation of the arterial or venous blood when measured in the large central arteries and veins. Noninvasive imaging of ischemia lacks the immediacy that allows for early intervention or real-time feedback to other devices such as pacemakers.

Non-implantable ischemia sensors are known. For example, U.S. Pat. No. 6,532,381 teaches the detection of ischemia using externally measured electrical (EKG) monitoring and microprocessor control. However, such devices monitoring multiple external sites using wire leads placed upon the chest wall are not designed for implantability, which requires that issues of size, power consumption, biocompatibility, and robustness over time be optimized alongside sensing performance, a non-trivial task.

Implantable sensors are also well known. However, implantable sensors designed to detect ischemia are rare in the art, and none of these detect tissue ischemia directly. For example, U.S. Pat. No. 5,135,004, US Appn 2004/0122478, and WO 00/64534 predict the presence of ischemia based upon the electrical (EKG), blood pressure, local pH, and/or physical (acceleration during contraction) characteristics of the heart, while U.S. Pat. No. 6,527,729 discloses an implantable acoustic sensor that responds to heart failure by changes in the sound of the heartbeat. Further, U.S. Pat. No. 5,199,428 and US Appn 2004/0220460 teach implantable devices to monitor blood oxygenation (venous blood and arterial blood, respectively), in the latter case specifically rejecting local tissue saturation from encapsulation, thus teaching away from direct tissue monitoring. For reasons to be outlined in more detail later, such non-tissue blood oxygenation (whether arterial or venous) is insensitive to tissue ischemia, and is at best an indirect measure of tissue ischemia. For each of the devices above, then, ischemia is measured only by indirect and unreliable indicators of ischemia, such as by indicators of cardiac electrical, mechanical, and acoustic dysfunction. Another point to consider is that organs other than the heart are frequent sites of ischemia (such as in the kidney, liver, or gut), and the prior art is not directed to these other organs at all. Therefore, none of the above devices detect local tissue ischemia directly, nor can they be applied generally to any organ without regard to site.

All of the above devices are limited by being either non-implantable, by being at best an indirect measures of local tissue ischemia, or by being restricted to use in just one organ such as the heart due to the indirect measures of ischemia (such as sound or movement) which they employ.

None of the prior devices or methods allow for a direct detection of local tissue ischemia in a broad array of target sites using a long-term or short-term implantable system sensitive to local ischemia, Such a system has not been previously described, nor successfully commercialized.

SUMMARY OF THE INVENTION

The inventors have discovered that the site at which tissue ischemia occurs is always local, and that local tissue physiology in nearly every case will attempt to compensate for this local ischemia, producing a direct depression then partial compensation on the capillary hemoglobin saturation. This local effect is often not measurable using standard blood monitoring, and capitalizing on this local capillary effect allows for the design a highly localized, fully-implantable ischemia detector.

A salient feature of the present invention is that the detection and treatment of ischemia is aided by use of an implantable ischemia sensor.

Accordingly, an object of the present invention is to provide a fully-implantable ischemia detector.

In one aspect the invention provides a direct, quantitative measure or index of local tissue ischemia.

In another aspect the invention provides a short-term implantation, such as optical fibers within the heart muscle after bypass surgery, or an implant in the lung tissue for short-term monitoring after a transplant, or even a swallowable device for detecting ischemia in the gut as it passes through the enteric system.

The improved ischemia detection system as described has many advantages one or more of which are descipled below. While a number of advantages are set forth for illustrative purposes only, these advantages are not intended to limit the scope of the claims in any way.

One advantage is that a physician or surgeon can obtain real-time feedback regarding local tissue ischemia in high-risk patients, and to respond accordingly, while any injury remains reversible.

Another advantage is that this system may be safely deployed within a living body.

Another advantage is that the system can be actively coupled to a therapeutic device, such as a pacemaker, to provide feedback to the pacing function, or passively coupled to a therapeutic device, such as applied to a stent to monitor stent performance over time.

Another advantage is that the system may be constructed to detect ischemia using light, which allows for simple, safe, and non-electrical transmission of the measuring photons as required.

Another advantage is that the detection can be in the tissue itself, rather than removed from the site of ischemia. Sources of local tissue signals include but are not limited to capillary hemoglobin (not in the arterial or venous circulation but locally in the capillaries in the tissue), myoglobin (which is extravascular and within muscle cells in the tissue itself) and cytochrome (which is intracellular within the mitochondria of the cells of the tissue itself).

Another advantage is that use of broadband light can allow for determination of tissue ischemia using spectroscopy, and in particular differential spectroscopy, which allows for compensation of light scattering by tissues.

A final advantage is that ischemia sensing may be used to enable detection of many types of disease, such as tissue rejection, tissue infection, vessel leakage, vessel occlusion, and the like, many of which produce ischemia as an aspect of the disease.

There is provided an implantable device or system with broadband light source for generating light, and for delivering this light to a sample for the purpose of enabling spectroscopic ischemia detection. In some embodiments, the system uses a phosphor-coated white LED to produce continuous, broadband light from 400 nm to 700 nm, which is transmitted directly to a target site. Scattered light returning from the target is detected by a wavelength-sensitive detector, and a signal related to ischemia is generated using this wavelength-sensitive information via spectroscopic analysis. Finally, this signal is sent out from the device using radiofrequency (RF) transmission. Implantable systems incorporating the ischemia detection system and medical methods of use are described.

The breadth of uses and advantages of the present invention are best understood by example, and by a detailed explanation of the workings of a constructed apparatus, now in operation and tested in animals. These and other advantages of the invention will become apparent when viewed in light of the accompanying drawings, examples, and detailed description.

DETAILED DESCRIPTION OF THE INVENTION

Definitions

For the purposes of this invention, the following definitions are provided. These definitions are intended to be illustrative and exemplary. They are not intended to restrictively limit, by the absence of any specific illustrative example, the common-sense breadth of meaning of the terms to those skilled in the art. These definitions are as follows:

Implantable: Intended for implantation internally in a living body, such as into or between internal tissues. Implantable devices typically must be biocompatible (i.e., have a biocompatible exterior), or else the host subject's immune system will attack the implanted object or the device will have a toxic effect upon the host.

Implantable does not require any fixed duration. Implantable as used herein can mean short-term implantation, such as removable fibers inserted in the heart or lung, or a swallowable device such as an gastrointestinal ischemia monitor. Implantable as used herein may also be a long-term implantation, such as a pacemaker feedback system which monitors the heart or muscle, or a liver-based MEMS device that monitors for rejection.

Fully-Implantable: Complete implantation into a living body, without a physical connection to the external body. Fully-implantable devices may contain an embedded power supply, receive power from another implanted device (such as a pacemaker), or receive power from an external source such as via transcutaneous inductive coupling. Fully-implantable devices may still communicate with receivers external to the body via non-physical means, such as electromagnetic waves from RFID chips. An implantable system may be embedded long-term, such as buried deep within a body to monitor for organ rejection or cardiac ischemia. An implantable system may also be used short-term only, such as a swallowable pill that monitors for ischemic ulcers or polyps in the esophagus, stomach, intestines, and colon, and is passed via the rectum when the scanning is complete in a few hours to a few days.

Tissue: Material from a living animal, plant, viral, or bacterial subject, with an emphasis on mammals, especially humans.

Perfusion: The flow of blood to a tissue or region, which differs from tissue ischemia in that low flow does not guarantee ischemia.

Blood Oxygenation: The saturation of the hemoglobin in arterial and venous blood, which differs from tissue ischemia. Arterial blood can be 100% oxygenated, yet a blood clot in the coronary artery will produce severe ischemia despite the 100% arterial saturation. Similarly, a local occlusion may produce lethal local ischemia, while the average venous oxygenation is not lowered detectably due to the small contribution of that local tissue to the overall venous blood oxygenation.

Ischemia: A local condition of tissue in which the delivery of oxygen to the tissue is locally inadequate to meet its metabolic needs. Such conditions vary from tissue to tissue. For example, the brain has a high metabolic rate and is easily made ischemic, even during simple tasks such as deep thought and insight, unless there is a local and rapid increase in the baseline blood flow and oxygen delivery to the metabolizing cortical tissues. In contrast, the growing fetus is in a relative hibernation state, with very low oxygen needs in most tissues, and is more difficult to make ischemic. Early and mild ischemia is often evidenced by increases in the amount of oxygen extracted from the blood being delivered to the capillary bed, resulting in decreased tissue oxygenation. Later stage ischemia is evidenced by lactic acid formation and disturbed cellular metabolism that occurs when the simple compensatory mechanisms of the tissue (increase oxygen extraction, increase flow) are no longer sufficient to protect the tissue from the rising ischemia. Ischemia is therefore distinguished from perfusion (i.e., blood flow) in that low blood flow does not guarantee ischemia (such as during tissue cooling or in the fetus), nor does high flow rule out ischemia (such as during sepsis, fever, or intense work). Ischemia is a co-existing condition in many different types of illnesses, including sepsis, tissue rejection, heart attack, stroke, organ failure, diabetic disease, and other conditions.

Target: A material to be detected, imaged, or studied. In the accompanying examples, one target site is the intestine.

Target Signal: A sensed signal specific to the target. This signal may be enhanced through use of a contrast agent. This signal may be produced by scattering, absorbance, phosphorescence, fluorescence, Raman effects, or other known spectroscopy techniques.

Visible Light: Electromagnetic radiation from blue to yellow, namely with wavelengths between 400 nm and 625 microns, but especially those green to orange wavelengths between 475 and 600 nm where the absorbance by capillary hemoglobin (not in the arterial or venous circulation but locally in the capillaries in the tissue), myoglobin (which is extravascular and within muscle cells in the tissue itself) and cytochrome (which is intracellular within the mitochondria of the tissue itself) is the strongest.

Broadband Light: Light produced over a wide range of wavelengths sufficient to perform solution of multiple simultaneous spectroscopic equations. For tissue, a width of at least 40 nm is likely to be needed, while in the preferred embodiment a broadband white LED produces light from 400 nm to beyond 700 rim.

LED: A light emitting diode.

White LED: A broadband, visible wavelength LED, often comprised of a blue LED and a blue-absorbing broad-emitting phosphor that emits over a wide range of visible wavelengths. Other phosphors can be substituted. As used in the examples herein, any broadband LED could be used, even if not emitting over a full (white) spectrum. For example, a green LED emitting over a FWHM range of 100 nm would be considered to be broadband.

Light Source: A source of illuminating photons. It may be composed of a simple light bulb, a laser, a flash lamp, an LED, a white LED, or another light source or combination of sources, or it may be a complex form including but not limited to, a light emitter such as a bulb or light emitting diode, one or more filter elements, a transmission element such as an integrated optical fiber, a guidance element such as a reflective prism or internal lens, and other elements intended to enhance the optical coupling of the light from the source to the tissue or sample under study. The light may be generated using electrical input (such as with an LED), optical input (such as a fluorescent dye in a fiber responding to light), or any other source of energy, internal or external to the source. The light source may be continuously on, pulsed, or even analyzed as time-, frequency-, or spatially-resolved. The light emitter may comprise a single or multiple light emitting elements, such as a combination of different light emitting diodes to produce a spectrum of light.

Light Detector or Light Sensor: A detector that generates a measurable signal in response to the light incident on the detector.

Optical Coupling: The arrangement of two elements such that light exiting the first element interacts, at least in part, with the second element. This may be free-space (unaided) transmission through air or space, or may require use of intervening optical elements such as lenses, filters, fused fiber expanders, collimators, concentrators, collectors, optical fibers, prisms, mirrors, or mirrored surfaces and the like.

Embodiments of the device and system will now be described.

Figure 1:
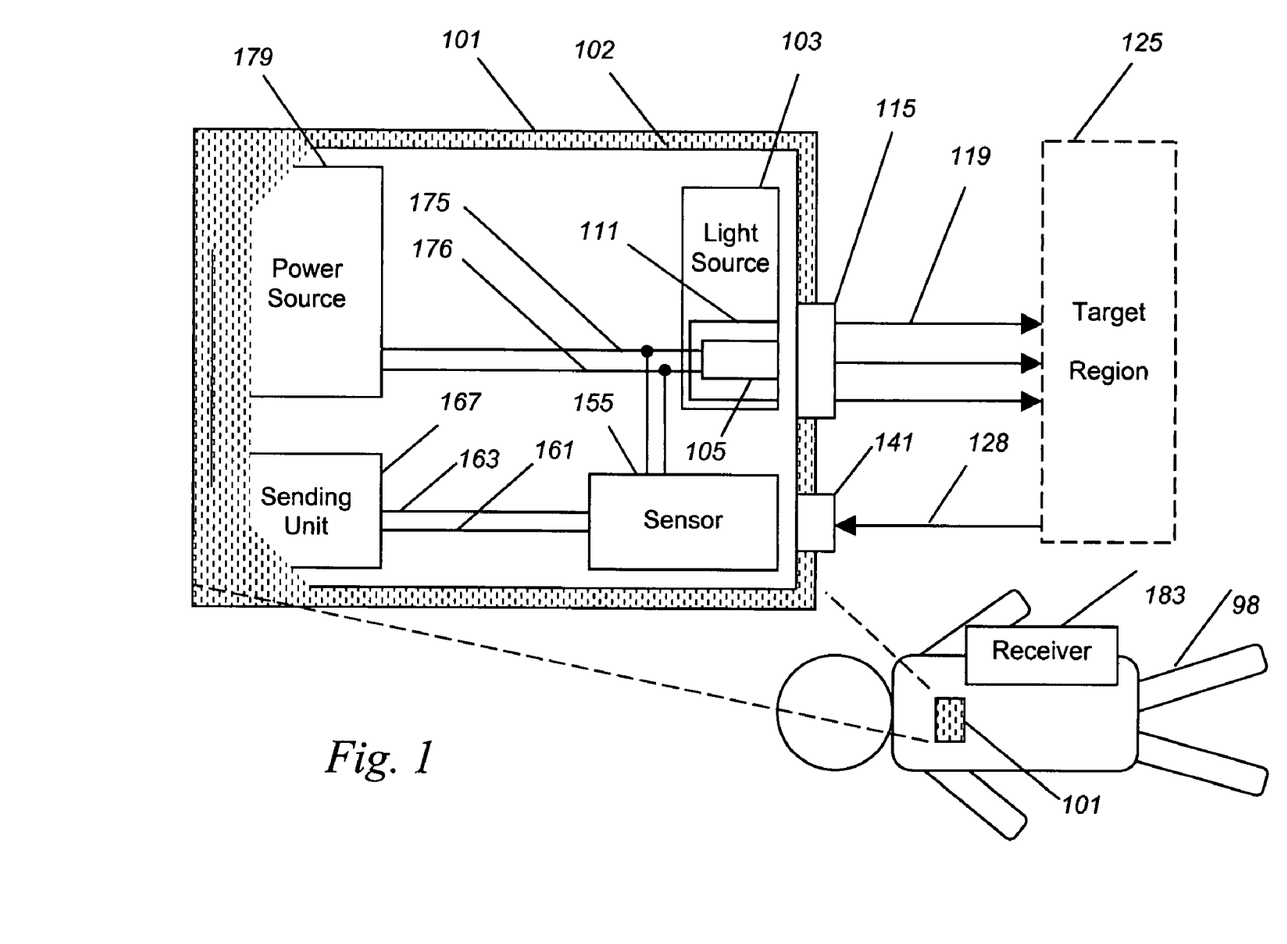
FIG. 1 is a schematic diagram of an implantable tissue ischemia detector incorporating a white LED and constructed in accordance with embodiments of the invention.

FIG. 1 shows device 101 implanted into the chest wall of patient 98. Of note, patient 98 is shown for illustrative purposes, and is not considered a part of the invention. A cutaway schematic of device 101 showing the interior of implantable device 101 is shown at the top of FIG. 1. Device 101 is surrounded by biocompatible exterior 102. Typically, exterior 102 is constructed from approved Class VI materials as recognized by the U.S. FDA or other medical device regulatory agencies, such as polyethylene or surgical steel. Portions of the sensor, power supply, light source, or transmitter may protrude as needed from this shell within the spirit of this invention, provided that the protruding parts themselves are biocompatible.

Within device 101, light source 103 is illustrated in its component parts. In some embodiments, broad spectrum white light is emitted by a high conversion-efficiency white LED source 105 (in this case, The LED Light, model T1-3/4-20W-a, Fallon, Nev.). In the exemplary embodiments, diode source 105 is embedded into a plastic beam-shaping mount using optical clear epoxy 111 to allow light generated in LED 105 to be collimated, thus remaining at a near-constant diameter after passing through optical window 115 to leave device 101. Light then is able to pass forward as shown by light path vectors 119, with at least a portion of this light optically coupled to target region 125. Note that while target region 125 may be in some instances a living tissue, the tissue itself is not considered to be a claimed part of this invention.

A portion of the light reaching target 125 is absorbed by ischemia in the tissue and another portion is backscattered and returns as to device 101, as shown by light path vectors 128, to optical collection window 141. Collection window 141 in this embodiment is a glass, plastic, or quartz window, but can alternatively be merely an aperture, or even be a lens, as required. Light then strikes sensor 155, where it is sensed and detected.

Sensor 155 may comprise a number of discrete detectors configured to be wavelength-sensitive, or may be a continuous CCD spectrometer, with entry of light by wavelength controlled by gratings, filters, or wavelength-specific optical fibers. In any event, sensor 155 transmits an ischemia signal related to the detected light backscattered from target 125, producing an electrical signal sent via wires 161 and 163 a sending unit 167, such as a transmitter chip. The signal transmitted by the sending unit 167 is received by the receiver 183 where it can be further processed to provide a display.

In one embodiment, light source 103 also has two electrical connections 175 and 176, connecting light source 103 to power source 179. In one embodiment, power source 179 is an inductive power supply, capable of receiving an inductive field from externally powered coil and RFID receiver 183 (FIG. 2) placed outside of the body, in order to produce power for device 101 as required. Note that external powered coil 183 is shown for the purposes of example and illustration, but is not considered a required part of this invention. Alternatively, source 179 could merely be a long-lived implantable battery, in which case an external powered coil may not be required at all.

Operation of the device may now be described.

Device 101 is implanted in a patient, for example in the chest wall of a patient undergoing coronary artery repair for heart disease. The device may measure the muscle directly, or it can be placed at a distance. In the latter case, vectors 119 are fiber optics extended from device 101 and into close proximity to the target heart muscle, sufficient for optical coupling. Then the patient is allowed to heal after surgery, and the implantable device is left inside the patient's body, without a direct physical connection to the outside world.

Figure 2:
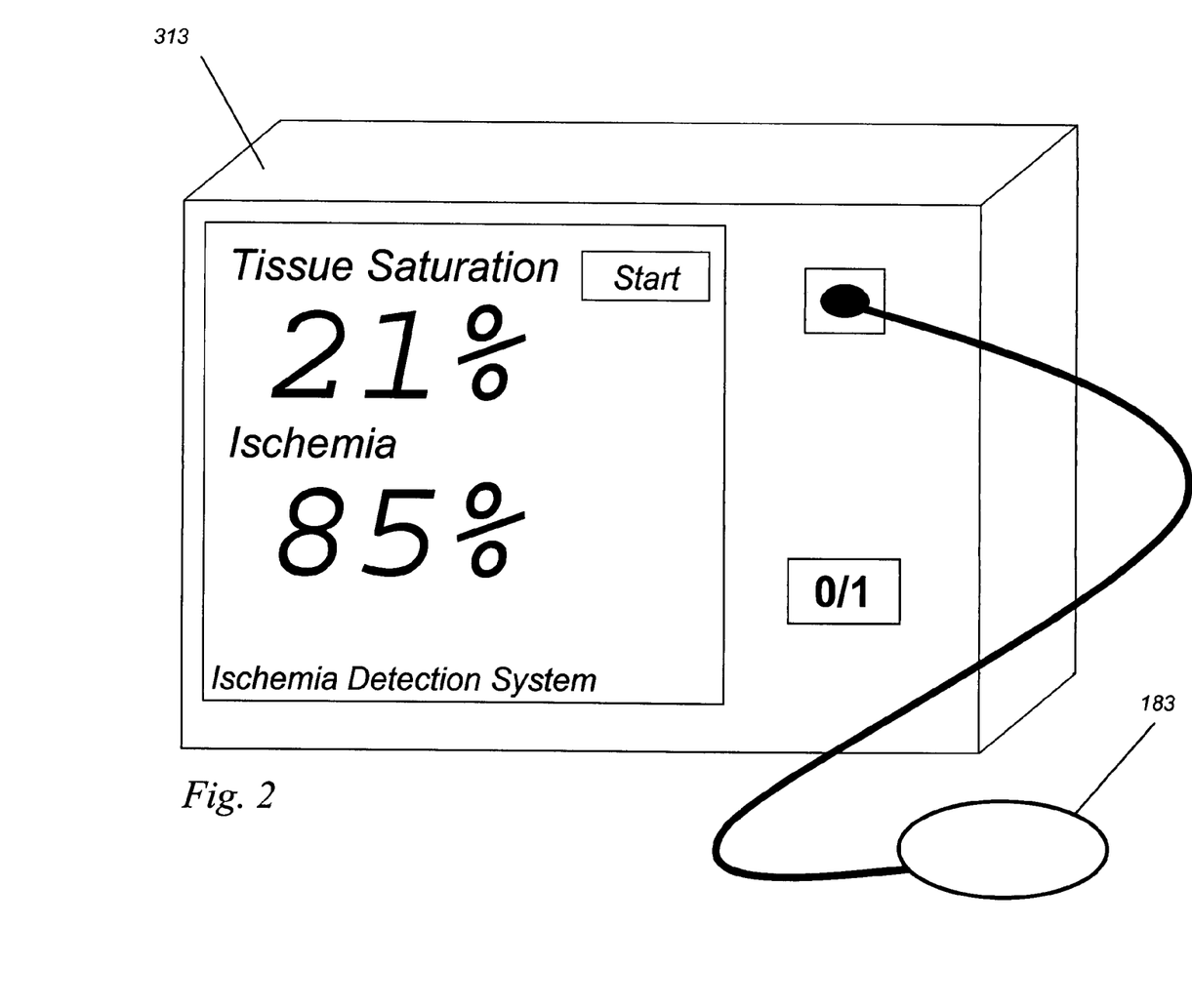
FIG. 2 is a schematic of an external coil, for powering the implantable device and for receiving a signal related to the presence or degree of tissue ischemia, attached to an external monitor system.

In this example, device 101 is normally powered down and in a resting (off) state. At some point, it is desired to test the target heart muscle for the presence of ischemia. As shown in FIG. 2, external inductive coil 183 is connected to external monitor is brought into close proximity to the chest wall over the site of implantation of device 101. Referring back to FIG. 1, through inductive coupling external coil 183 induces a current in inductive power source 179 located within device 101, producing sufficient power for device 101 to power up and turn on. Light source 103 begins to illuminate the target 125, in this case heart muscle. Sensor 155, which is an embedded spectrophotometer in some embodiments, receives backscattered light, resolves the incoming light by wavelength, a marker of ischemia. The result of this determination is sent to sending unit 167, which in the exemplary embodiment is an RF transmitter that sends the sensed signals to external RFID receiver 184. There, the signal received by receiver 184 may be processed for the oxygenation of the hemoglobin in the terminal capillary beds, a marker of ischemia, by external monitor 313, as shown in the data collected and plotted under the Example section, below. An example of a system for indicating oxygenation is described in U.S. Pat. No. 5,987,346, incorporated herein by reference.

Once the measurement is completed, external coil 183 is moved away from device 101, and device 101 powers down and returns to a resting state.

In an alternative embodiment, power source 179 may be charged during proximity to external coil, or have an internal battery source, allowing device 101 to operate when external coil 179 is not present. Sending unit 167 may then transmit without being directly queried, such as in response to a dangerous level of ischemia.

The light sensor which resolves the incoming light by wavelength and sends a signal to the sending unit has been mentioned, and will now be more fully described with reference to FIGS. 3A to 3E. In one form, FIG. 3A, the sensor 155 is merely single photodiode 411 and processing electronics 413. Photodiode 411 is made wavelength sensitive through the design of LED 105 as a cluster of LEDs of different wavelengths, each emitting at a different time or modulation frequency to allow decoding of the illuminating wavelength by photodiode 411 and processing unit electronics 413. Alternatively, sensor 155 may comprise a set of different photodiodes 421A through 421N, FIG. 3B, each with filters 425A through 425N, allowing each photodiode to be sensitive to only one wavelength range, again allowing decoding of the sensed light by wavelength by processing unit electronics 427. Alternatively again, sensor 155 may be single photodiode 431 with electronically variable filter 433, FIG. 3C, allowing the wavelength transmitted to be selected and processed by processing unit electronics 435.

Figure 3A:
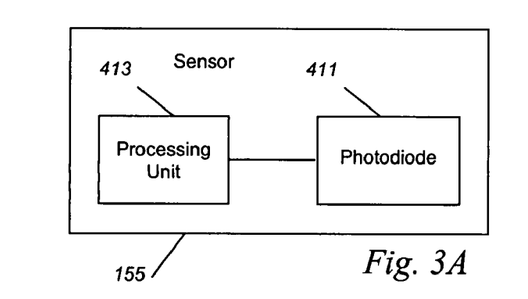
FIGS. 3A to 3E shows five exemplary schematics of the optical sensor unit.
Figure 3B:
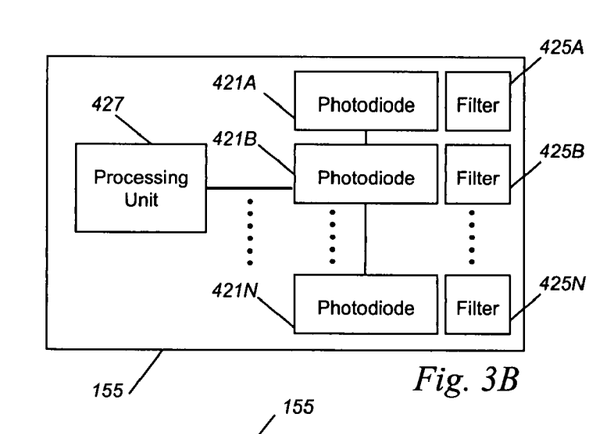
Figure 3C:
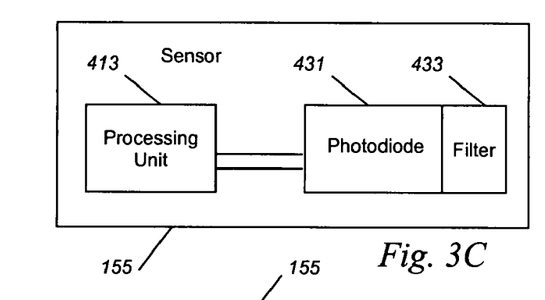
Figure 3D:
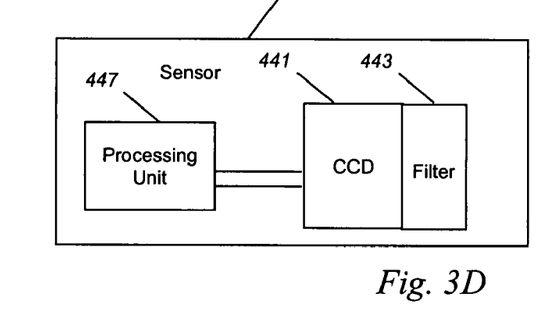
Figure 3E:
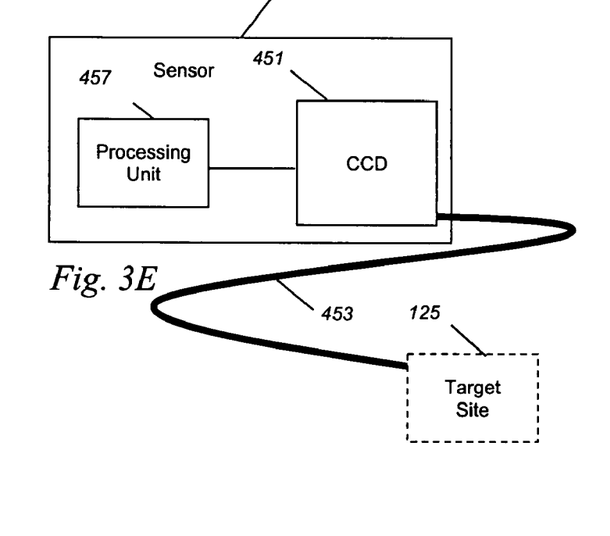

Still referring to FIGS. 3A to 3E, in other configurations, sensor 155 may be CCD chip 441 with filter window 443, FIG. 3D, that varies over its length, allowing only certain wavelengths to reach each portion of CCD 441, allowing decoding of the illuminating wavelength by processing unit electronics 447. Finally, in the preferred embodiment, FIG. 3E, sensor 155 comprises CCD chip 451 with optical fibers 453 attached to CCD 451 in a linear array. Fibers 453 are manufactured such that each fiber has a different interference coating on end 454, allowing each fiber to transmit a different narrow wavelength range, allowing decoding of the illuminating wavelength by processing unit electronics 457. Fibers 453 are biocompatible and can extend outside of device case 102, allowing device 101 to be placed remotely the target to be monitored, and for the free end of fibers 453 to be placed in proximity to target 125.

EXAMPLE

The breadth of uses of the present invention is best understood by example. This example is by no means intended to be inclusive of all uses and applications of the apparatus, merely to serve as a case study by which a person, skilled in the art, can better appreciate the methods of utilizing, and the scope of, such a device.

In this example, an optical sensor, similar in basis of operation to device 101, is implanted into abdomen of a patient undergoing colon surgery. In this case, the animal receives heart-lung bypass, such that the blood flow and oxygen content of the blood is exactly controlled by a bypass specialist rather than by the animal's own heart and lungs, affording the ability to create and resolve ischemia at will. An aortic Doppler probe is placed, which measures the delivery of blood to tissue. In this case, when the rate of the pump is lowered to zero flow, ischemia must exist in the tissues being monitored.

Analysis of the tissue ischemia is performed by broadband, visible light, differential spectroscopy. In this technique, the first differential (for example) of the wavelength vs. intensity curve sent from the sending unit is processed to remove many of the effects caused by light scattering by the local tissue, and the resultant signal is analyzed using a least-squares minimization of the fitting error to known components of the tissue (such as myoglobin, capillary hemoglobin, or cytochromes).

The signal that is measured is a function of the presence, absence, or risk, or degree of ischemia. This can have clinical implications and applications in many different medical areas, such as impending risk of tissue death (as seen in the colon study above), impending risk of organ rejection (as inflammation results in increased total blood content, while potentially reducing oxygenation) cardiac function (as improved cardiac function is associated with a body-wide improvement in tissue ischemia as well as a likely improvement in myocardial ischemia), treatment efficacy for arterial or venous vascular disease (as the real-time effects of such interventions on tissue oxygenation adequacy can be used as a treatment signal to guide chemical and physical interventions), risk of renal damage (as kidney failure is often the result of acute or chronic reduced oxygen delivery), risk of brain injury (as stroke is often the result of acute and chronic reduced oxygen delivery), risk of colon death (as the colon does not have a large capacity to increase blood and oxygen delivery in times of stress over baseline), risk of limb amputation (as limbs with good capillary saturation are more likely to heal and not require amputation), risk of ulcer healing (as G.I. and diabetic ulcers are more likely to heal if ischemia is not the only ongoing problem), and risk of critical limb ischemia (as limb salvage is always better if possible, but delays resolution of ischemia and presents a risk to the patient if delayed when amputation is required).

Figure 4:
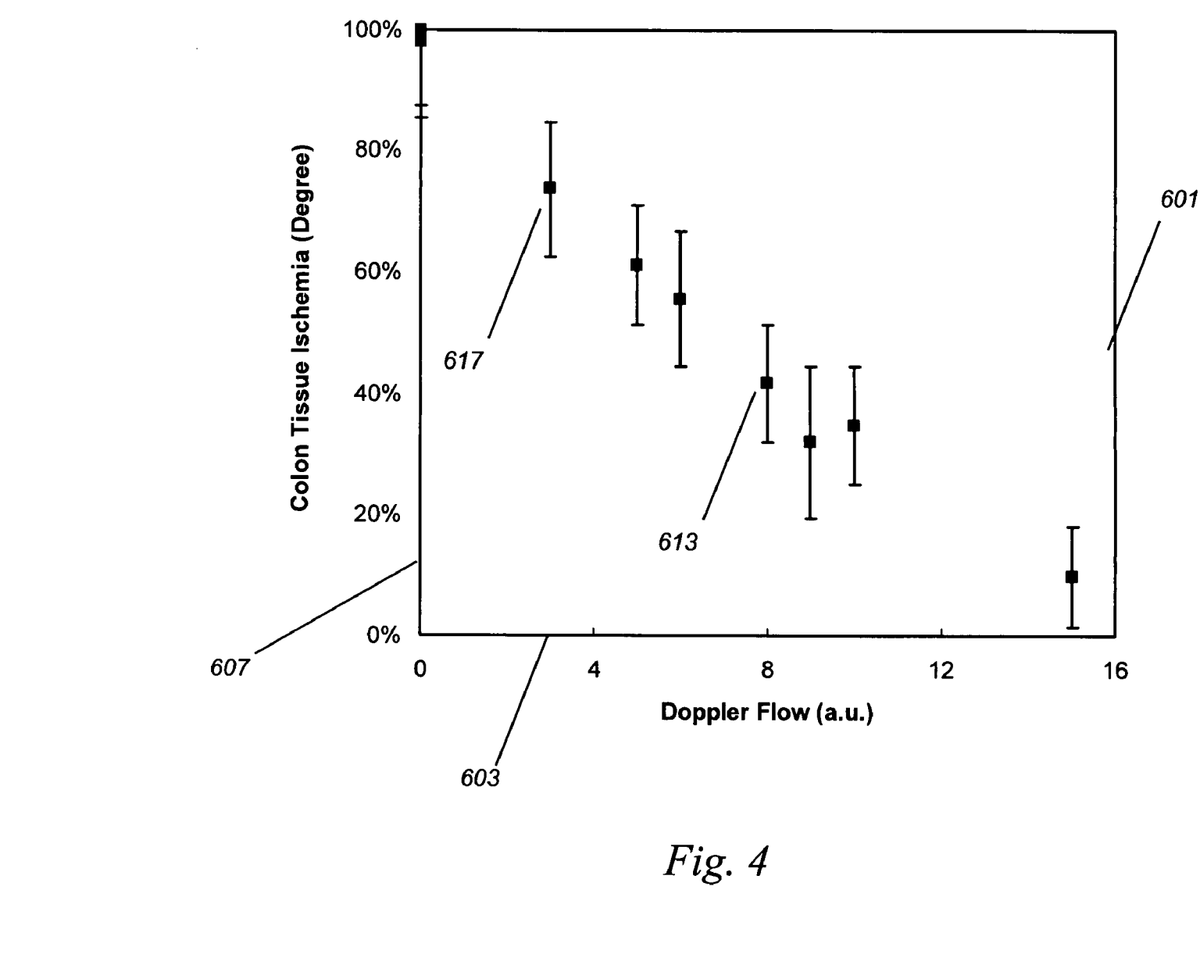
FIG. 4 shows data from the colon of a live subject during periods of low systemic blood flow, which led to local ischemia, as collected and analyzed in real time by a medical monitor constructed in accordance with embodiments of the invention.

As shown in FIG. 4, the creation of graded ischemia is detected by the present invention. In graph 601, the flow detected by the Doppler probe is plotted on horizontal axis 603 versus the presence of ischemia as detected by the present invention using optical spectroscopy plotted on vertical axis 607. Data are plotted as means with standard error bars 613. As can be seen on graph 601, when the blood flow to the gut is reduced to zero, the detection of the presence of ischemia rises to 100%, shown at data point 617.

It is important to note that the measurement of flow/perfusion alone, or the measurement of blood oxygenation (not tissue oxygenation, but oxygenation of the arterial blood) alone are not sufficient to detect the condition of ischemia. Ischemia is diagnosed by low local tissue oxygenation, not blood oxygenation or flow. In some cases, arterial blood may be well oxygenated, but the delivery of this arterial blood to the tissue is insufficient (such as with a blood clot); in this case the tissue is indeed ischemia while the arterial blood oxygenation is normal. Blood flow also differs from a direct measure of ischemia. For example, in a cooled patient on heart-lung bypass, blood flow may be very, very low; however, the cooled tissues, whose oxygen need has been reduced by the low temperature, are not ischemic. Similarly, a chronically ischemic heart "hibernates" in order to reduce its own oxygen need, and may not be ischemic at reduced flow. In the above animal study example, flow was controlled sufficiently to allow for a low or zero flow to be consistent with ischemia, but such conclusions cannot be always made so clearly in the living non-experimental subject.

Also, in the example above, power was provided to the device externally. However, as noted earlier, an integrated battery or set of batteries can provide power from within the device, reducing cost of the connection tip. An added advantage of this battery-based approach is that it removes the need for electrical connection to the light source, as an added safety feature.

In this example, the signal detected from the tissue was a hemoglobin absorbance signal derived from the capillary bed. While absorbance is ideal for hemoglobin analysis, as described in the preferred embodiment, other interactions may be preferable for other measurements. The interaction with the illuminating light that provides the contrast can include absorbance, polarization, optical rotation, scattering, fluorescence, Raman effects, phosphorescence, or fluorescence decay, and measures of a contrast effect may reasonably include one or more of these effects. Other tissue components could be measured, including NADH, NADPH, cytochromes in their oxidized and reduced forms, or even ischemia or oxygen sensitive dyes. Next, when monitoring muscle such as the heart, myoglobin is another protein whose saturation is related to the presence or absence of ischemia. In such cases, a combination of hemoglobin in the capillaries as well as myoglobin in the heart, or just myoglobin in the heart myocytes, can serve as a marker of ischemia. Last, an injectable dye, sensitive to local ischemia, can be used to generate an optical signal directly related to the presence of ischemia, such as by changing color in response to mitochondrial membrane charge or in response to intracellular pH. Such use of dyes to label cells in vivo with optical dyes has been demonstrated in vivo by several groups, and the coupling of an ischemia sensitive dye to use of the present invention to detect ischemia (and conditions which are a function of ischemia) would fall within the spirit of the present invention.

We have discovered an implantable ischemia detector for detecting local tissue ischemia in a quantitative and enabling manner in a broad array of target sites. In some embodiments a device is provided comprising a phosphor-coated white LED and integrated collimating optics conFIG.d to produce continuous, broadband light from 400 nm to 700 nm in a collimated beam, which is then directly transmitted to a target site. Light backscattered by the target site is collected by a sensor, allowing for a direct measure of ischemia to be determined, and subsequently transmitted by a sending unit. Power is provided by an internal power source, which may in turn be itself powered by an external inductive coil that is brought in proximity to the implanted device in order to provide energy as needed. The entire implantable device is encapsulated by a biocompatible shell to add long-term safety while implanted. Used alone, or in combination with an estimate of arterial oxygenation, venous oxygenation, or even of blood flow, this device allows for an index of ischemia to be determined without additional invasiveness beyond the initial implantation. The present device may be interrogated using inductive technology and RF coupling. Implantable devices incorporating the ischemia system, and medical methods of use, are described. This device has immediate application to several important problems, both medical and industrial, and thus constitutes an important advance in the art.

What is claimed is:

1. An implantable device comprising:
a light source for illuminating a target with light;
a sensor configured so as to detect light backscattered substantially from local capillary and extravascular tissue within the target site onto said sensor and to provide a tissue oxygenation output signal that is a direct function of the presence or degree of internal tissue ischemia based at least on said light backscattered from said site;
a power source configured to supply energy to said sensor, and said light source; and
an exterior shell enclosing said power source, light source, and sensor configured so as to be biocompatible with respect to implantation internally wherein said external shell is a swallowable capsule for passage through the gastrointestinal system.

2. The implantable device of claim 1, wherein said light source is a broadband white LED.

3. The implantable device of claim 1, wherein said sensor is a CCD configured so as to be wavelength sensitive.

4. The implantable device of claim 1, wherein said output signal is generated using differential spectroscopy.

5. The implantable device of claim 1, wherein said power source is an inductive coil for receiving power.

6. The implantable device of claim 1, wherein said measure of internal tissue ischemia is a function selected from the list of functions comprising impending risk of tissue death, impending risk of organ rejection, cardiac function, treatment efficacy for arterial or venous vascular disease, risk of renal damage, risk of brain injury, risk of colon death, risk of limb amputation, risk of ulcer healing, or risk of critical limb ischemia.

7. The device of claim 1, further comprising a sending unit for receiving the output signal and transmitting said output signal.

8. The implantable device of claim 7, wherein said output signal is a function of a measure selected from at least one of a list of measures comprising tissue capillary hemoglobin saturation, cellular myoglobin saturation, and intracellular mitochondrial cytochrome saturation.

9. The implantable device of claim 7, wherein said sending unit is comprised of any one or more of an RF transmitter, an RFID chip, or an optical fiber.

10. An implantable device comprising:
a light source for illuminating a target with light;
a sensor configured so as to detect light backscattered substantially from local capillary and extravascular tissue within the target site onto said sensor and to provide a tissue oxygenation output signal that is a direct function of the presence or degree of internal tissue ischemia based at least on said light backscattered from said site;
a power source configured to supply energy to said sensor, and said light source;
an exterior shell enclosing said power source, light source, and sensor configured so as to be biocompatible with respect to implantation internally; and
a sending unit for receiving the output signal and transmitting the output signal, wherein said sending unit is coupled to an implanted pacemaker, for the purpose of real time feedback.

11. The implantable device of claim 10, wherein said external shell is a fully-sealed biocompatible shell for implantation in an organ or tissue.

12. The implantable device of claim 10, wherein said measure of tissue ischemia is a function selected from the list of functions comprising impending risk of tissue death, impending risk of organ rejections, cardiac functions, treatment efficacy for arterial or venous vascular disease, risk of renal damage, risk of brain injury, risk of colon death, risk of limb amputation, risk of ulcer healing, or risk of critical limb ischemia.

13. The implantable device of claim 10, wherein said light source is a broadband white LED.

14. The implantable device of claim 10, wherein said sensor is a CCD configured so as to be wavelength sensitive.

15. The implantable device of claim 10, wherein said output signal is a function of a measure selected from at least one of a list of measures comprising tissue capillary hemoglobin saturation, cellular myoglobin saturation, and intracellular mitochondrial cytochrome saturation.

16. The implantable device of claim 10, wherein said output signal is generated using differential spectroscopy.

17. The implantable device of claim 10, wherein said power source is an inductive coil for receiving power.

18. The implantable device of claim 10, wherein said sending unit is comprised of any one or more of an RF transmitter, an RFID chip, or an optical fiber.

* * * * *